(12) United States Patent
Linares

(10) Patent No.: US 8,439,856 B2
(45) Date of Patent: May 14, 2013

(54) COMPOSITE PLASTIC RIGID WALKING CAST WITH CUSHIONED INTERIOR SUPPORTS

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 291 days.

(21) Appl. No.: 12/557,562

(22) Filed: Sep. 11, 2009

(65) Prior Publication Data

US 2010/0069804 A1 Mar. 18, 2010

Related U.S. Application Data

(60) Provisional application No. 61/096,439, filed on Sep. 12, 2008.

(51) Int. Cl.
  *A61F 5/00* (2006.01)
  *A61F 5/37* (2006.01)

(52) U.S. Cl.
  USPC ............... 602/16; 602/23; 128/882

(58) Field of Classification Search ........... 602/5, 12, 602/16, 23, 26–28; 128/882; 5/624
  See application file for complete search history.

(56) References Cited

U.S. PATENT DOCUMENTS

| | | | |
|---|---|---|---|
| 4,057,056 A | 11/1977 | Payton | |
| 4,409,689 A * | 10/1983 | Buring et al. | 2/22 |
| 4,494,534 A | 1/1985 | Hutson | |
| 4,884,561 A * | 12/1989 | Letson, Sr. | 602/16 |
| 4,888,225 A | 12/1989 | Sandvig et al. | |
| 5,078,128 A | 1/1992 | Grim et al. | |
| 5,176,623 A | 1/1993 | Stetman et al. | |
| 5,207,637 A | 5/1993 | Janke et al. | |
| 5,286,249 A * | 2/1994 | Thibodaux | 602/12 |
| 5,306,230 A | 4/1994 | Bodine | |
| 5,707,347 A * | 1/1998 | Bixler | 602/26 |
| 6,024,713 A | 2/2000 | Barney | |
| 6,377,178 B1 | 4/2002 | DeToro et al. | |
| 6,936,020 B2 | 8/2005 | Davis | |
| 6,974,431 B2 | 12/2005 | Jensen et al. | |
| 7,147,612 B2 * | 12/2006 | Molino et al. | 602/26 |
| 7,762,972 B2 * | 7/2010 | Cho | 602/16 |
| 2006/0167396 A1 * | 7/2006 | Berger | 602/23 |
| 2008/0039756 A1 * | 2/2008 | Thorsteinsson et al. | 602/23 |

FOREIGN PATENT DOCUMENTS

WO   WO-9004372 A1   5/1990

* cited by examiner

*Primary Examiner* — Patricia Bianco
*Assistant Examiner* — Ophelia A Hawthorne
(74) *Attorney, Agent, or Firm* — Gifford, Krass, Sprinkle, Anderson & Citkowski, P.C.; Douglas J. McEvoy

(57) ABSTRACT

A walking cast having an upper cage assembleable over an upper leg and a lower cage assembleable over a lower leg and hingedly secured to the upper cage approximate a wearer's knee. A foot sole support is connected to the lower cage which includes lower angled supports for engaging side locations of the sole in a further hinged connection. Each of the upper and lower cages include a rear positioned fixed support with a second forward and hingedly connecting door. A plurality of cushioning supports secure to inner facing locations associated with each of the upper and lower cages.

14 Claims, 9 Drawing Sheets

COMPOSITE PLASTIC RIGID WALKING CAST WITH CUSHIONED INTERIOR SUPPORTS

CROSS REFERENCE TO RELATED APPLICATIONS

The present application claims priority of U.S. Provisional Application Ser. No. 61/096,439 filed Sep. 12, 2008.

FIELD OF THE INVENTION

The present invention relates generally to a rigid supporting walking cast. More specifically, the present invention teaches both lighter and heavier duty rigid walking cast constructions, in each case for providing improved and more comfortable support than with heavier walking casts made of a settable material.

DESCRIPTION OF THE PRIOR ART

The prior art is documented with examples of walking cast constructions, such usually including the provision of a pre-applied and settable/hardenable material, such as a plaster or the like which is often formed directly over a wearer's bare skin, and which may also incorporate some form of underside sole support. Disadvantages associated with such materials include patient discomfort (itching), their relatively greater weight and associated bulkiness, as well as the greater time and inconvenience associated with the formation and setting of the cast.

SUMMARY OF THE PRESENT INVENTION

The present invention discloses a quick assembled and cushioning walking cast having an upper cage assembleable over an upper leg of a wearer, with a lower cage assembleable over a lower leg of the user and hingedly secured to the upper cage approximate a wearer's knee. A foot sole is connected to the lower cage and upon which a wearer's foot is supported.

Each of the upper and lower cages include a plurality of interconnecting length and width extending supports and further include first and second assembleable and substantially semi-cylindrical clamshell sections, such as each further including a rear positioned and fixed support with a second forward and hingedly connecting door. Lower angled supports extend from the lower cage and which engage side locations of the sole, further such as in a hinged connection. Other features include a plurality of cushioning supports secured to inner facing locations associated with each of the upper and lower cages, with at least one of the cages being width adjustable.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
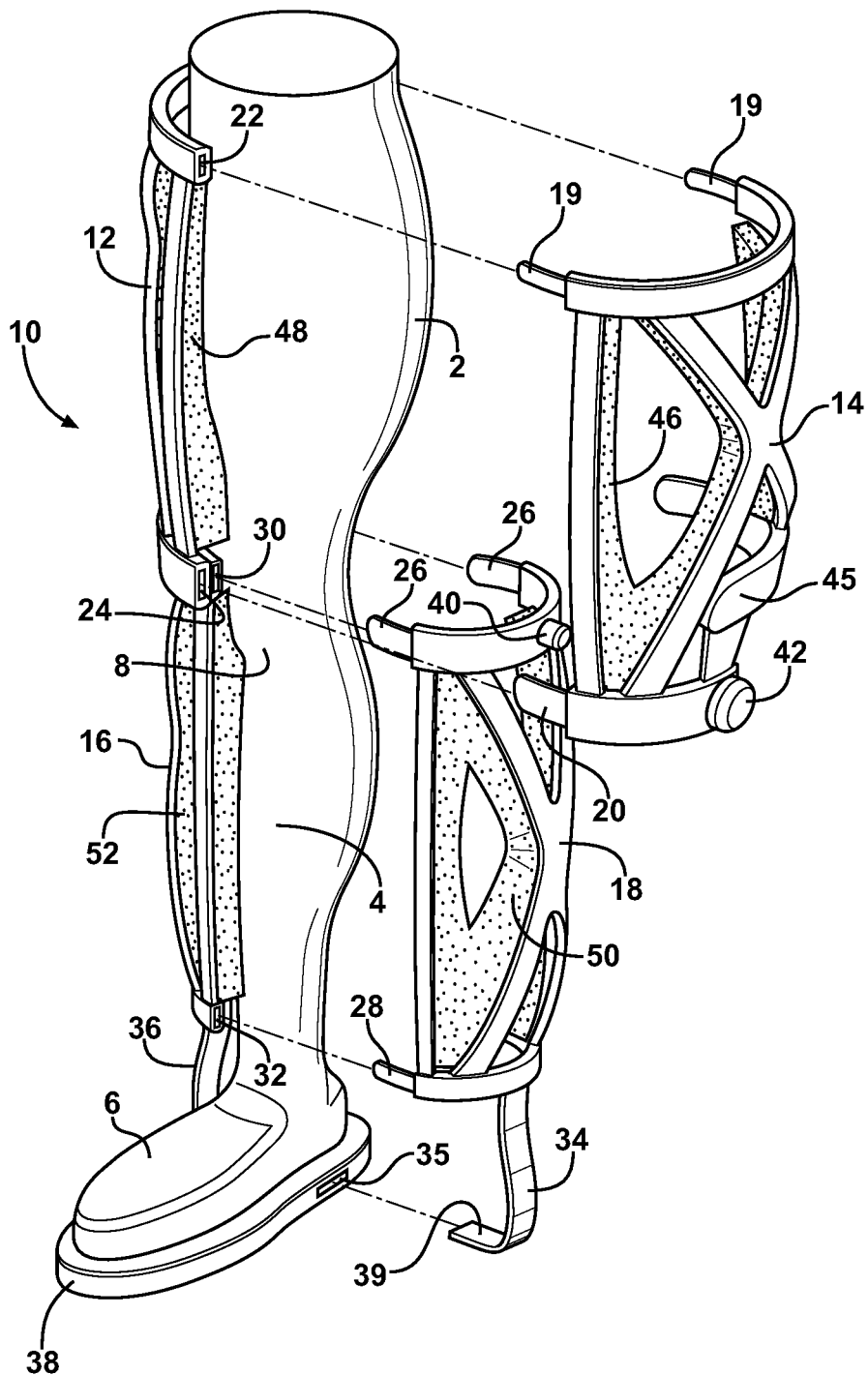
FIG. 1 is a partially exploded view of the composite plastic and rigid walking cast with cushioned inner supports according to a first preferred embodiment of the present inventions.

Referring now to FIG. 1, a partially exploded view is shown at 10 an assembleable and composite plastic and rigid walking cast with cushioned inner supports according to a first preferred embodiment of the present inventions. More specifically, the variant 10 (also shown in various assemblies illustrations FIGS. 2-4), constitutes a first lighter cast variant, with the subsequently described embodiment of FIGS. 5-9 disclosing a second heavier duty cast construction.

Figure 5:
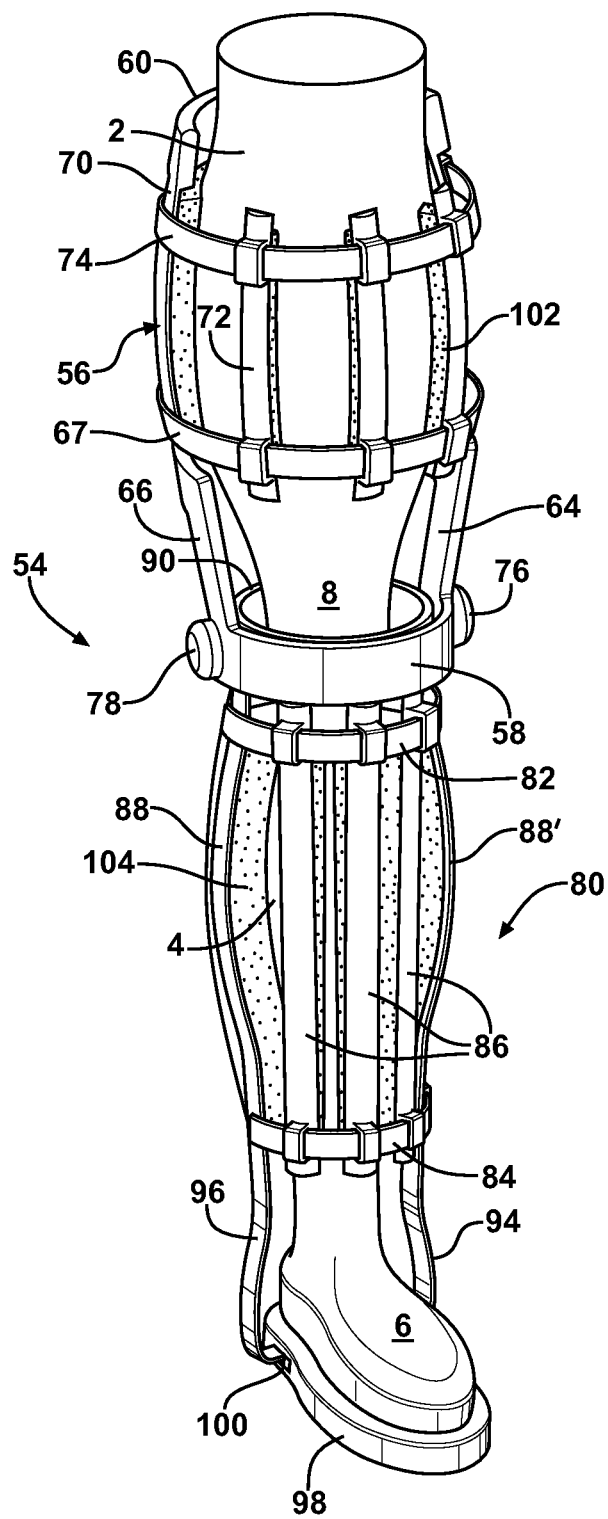
FIG. 5 is a perspective view of the composite plastic and rigid walking cast according to a second preferred embodiment of the present invention.
Figure 6:
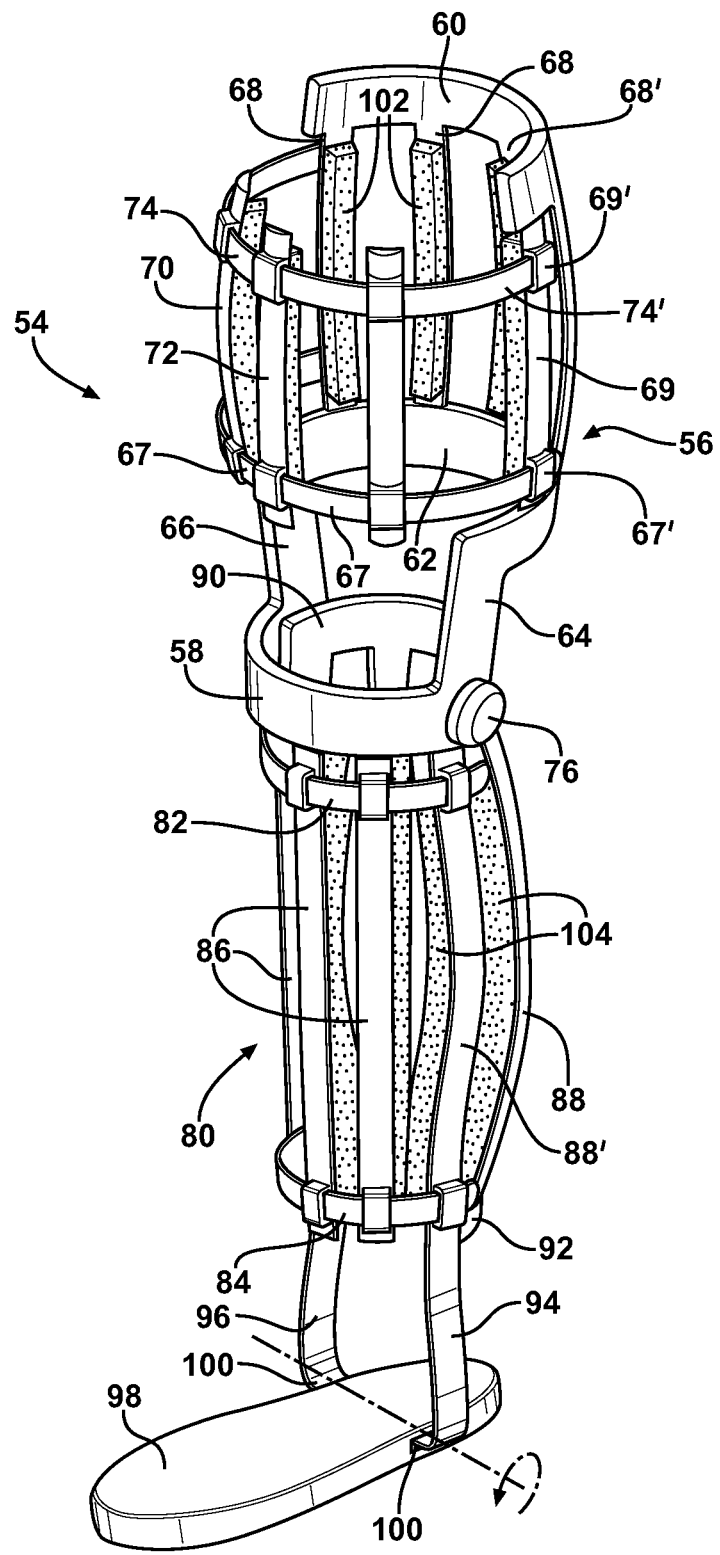
FIG. 6 is a rotated perspective view of the walking cast variant of FIG. 5 and further illustrating the manner in which the front cage portions associated with the upper and lower leg subassemblies are opened to allow for installation of the same.

The quickly assembleable constructions shown in each of FIGS. 1 and 5 are placed upon a wearer's leg, typically following an injury. As described previously, the present invention is an improvement over existing walking casts, such as which are usually formed over the wearer's bare skin. As will be described, the ability to quickly assemble/disassemble the cast provide for increased wearer comfort as compared to prior art molded walking casts.

Figure 2:
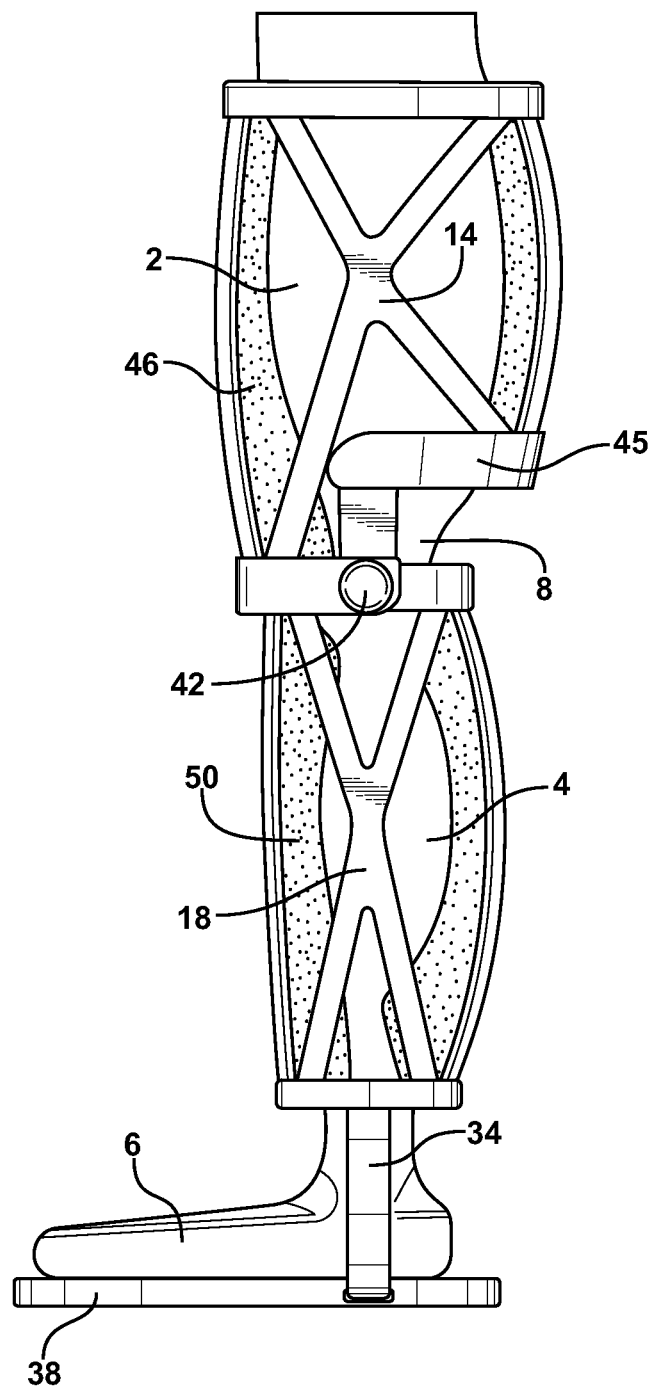
FIG. 2 is an assembled side view of the rigid walking cast shown in FIG. 1.
Figure 3:
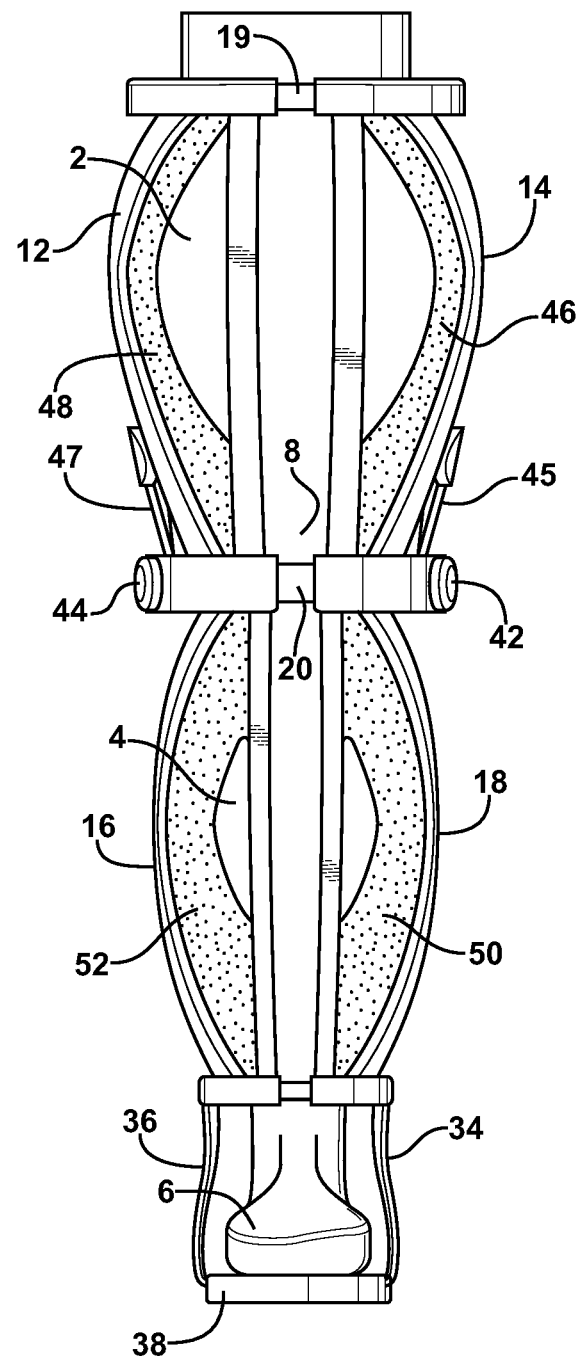
FIG. 3 is a front view of the cast shown in FIG. 2 and further illustrating the knee and ankle proximate located hinges/pivots.
Figure 4:
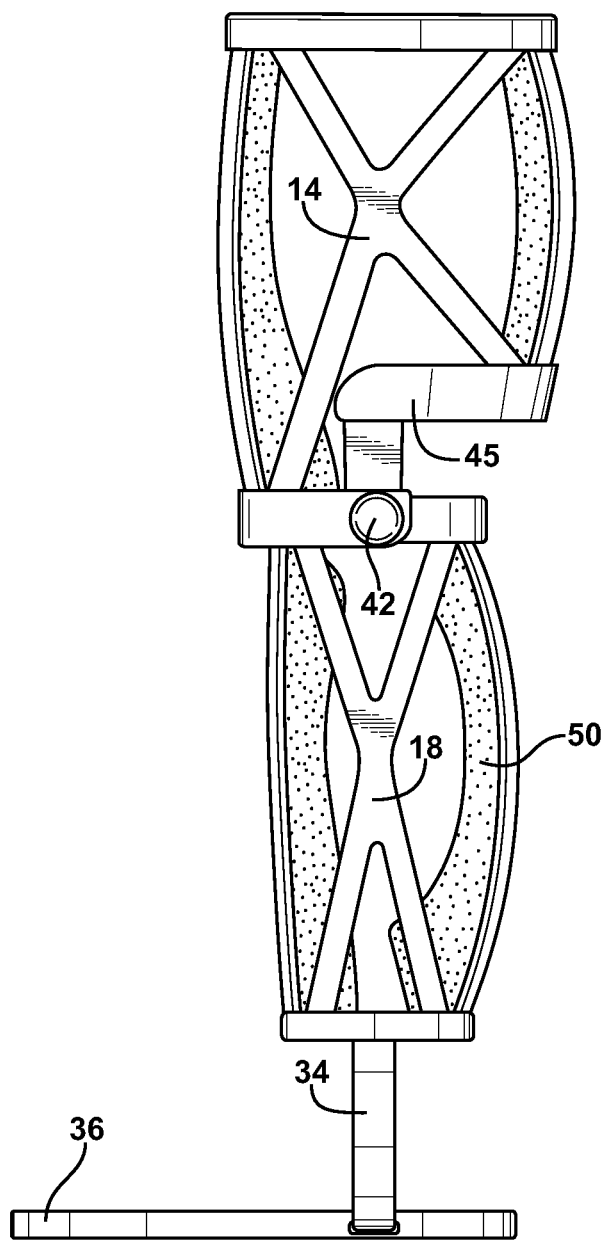
FIG. 4 is a side view of the rigid walking cast, similar to the environmental shown in FIG. 2, and without showing the user's leg.

As is also illustrated in each of the succeeding assembled drawings of FIGS. 2-4, the walking cast 10 of FIG. 1 includes an upper cage assembly having first 12 and second 14 assembleable sections, as well as a lower cage assembly likewise having first 16 and second 18 assembleable sections. Each of the individually assembleable sections is constructed of a semi-circular and elongate extending cage, having a generally grid shape with reinforcing and overlapping portions, as well as having opposingly extending and inter-engageable locations for assembling each of the upper and lower assemblies to respective upper (thigh) 2 and lower (calf) 4 portions of a wearer's leg. The material content of each cage section 12 & 14 and 16 & 18, includes such as a rigid plastic (i.e. composite) material, although it is understood that other material constructions, such as including lightweight aluminum or other metals/non-metals is also envisioned for use by one of ordinary skill in the art.

The upper assembly includes first and second pairs of engaging tabs (such as including attachment/adjustment straps) 19 and 20, these projecting from upper and lower ends of the second section 14 and which engage opposing recess/slot locations 22 and 24 defined in the first section 12. The lower assembly likewise includes first and second pairs of tabs (or adjustment straps) 26 and 28, projecting from upper and lower ends of the second section 18, and which engage opposing recess/slot locations 30 and 32 (again as best shown in FIG. 1) defined within the lower second section 16.

Support to a wearer's foot 6 is provide by lower angled supports 34 and 36, these extending respectively from bottom end locations of the lower assembleable sections 16 and 18, and which engage (such as again through the provisions of tab and slot arrangements or the like) with foot sole shaped rigid support 38. Shown at 35 in FIG. 1 is a selected lateral slot in the sole support 38, this providing a seating location for receiving a lower-most and inwardly angled inserting portion 39 associated with the selected lower support 34.

As also best shown in FIG. 1, articulation of an intermediate knee location (see at 8 in FIG. 1) is established by a hinged connection established between the upper and lower assembleable sections. Specifically, the lower assembly (with cage members 16 and 18) is first assembled about the wearer's lower leg portion 4. Illustrated at 40 in FIG. 1 is a laterally outwardly projecting support post which is formed at a midpoint/upper end location of the lower section 18. An identical support post is also understood to project in like fashion from the assembleable lower section 16, but is hidden from view.

The upper assembly (with cage members 12 and 14) is then assembled over the wearer's upper leg 2, with the cage members 12 and 14 being dimensioned so that their lowermost semicircular shaped portions overlap the uppermost semicircular shaped portions upon which the outwardly projecting support posts (again at 40) are formed. An inner seating hinge (one of which is shown at 42 for upper cage member 14 in FIG. 1) is defined upon the lowermost semicircular shaped portions of each of the cage members 12 and 14 and such that, upon assembly of the upper/outer cage members 12 and 14, the laterally projecting posts (one of which is again shown at 40 in FIG. 1) defined upon the midpoint upper end locations of the lower cage portions 16 and 18 seat within each of opposing and recessed undersides which are evident from the bulbous projecting hinges 42, in order to provide a degree of hinged supports between the upper and lower cage assemblies at the location proximate the wearer's knee 8.

Additional features include arcuately angled and configured supports, see at 45 and 47 in FIGS. 1 and 3, and which define a portion of the upper leg assembly cages 12 and 14. The supports, as best illustrated in the perspective of FIG. 1 by the support 45 associated with assembleable cage portion 14, are configured to support the rear thigh of the user, while permitting the lower leg 4 to bend an incremental degree without causing pain or discomfort to the wearer. In this fashion, the wearer is provided a limited degree of articulated mobility, at the knee location, and by virtue of the rigid construction of the upper and lower assemblies about the wearer's leg, in combination with the rigid foot sole support 38 exerted via the lower angled supports 34 and 36.

Additionally shown are inner positioned cushioned supports (such as foam supports) which are configured so as to be arranged along the inside recess surfaces of each of the upper and lower cage assembly members. The cushion supports include those shown at 46 and 48 for the upper assembleable cage members 14 and 12, as well as at 50 and 52 for lower assembleable cage members 18 and 16.

Each cushioned support 46 & 48 and 50 & 52 (or other suitably configured length and width configured supports) is configured such as in one non-limiting variant to include a similar overall grid shape relative to a surrounding cage section 12, 14, 16 and 18, and to seat within an interior recessed surface of each corresponding, and generally semi-cylindrical shaped, cage portion. Accordingly, and as shown throughout FIGS. 1-4, each of the cushioned supports 46-52 is further configured to exhibit a similar shape or pattern corresponding to that of each cage portion 12-18, such including an overlapping grid pattern or other such pattern which maximizes breathe-ability and comfort, while at the same time providing the requisite amount of wearer support. The cushioning/foam material can include any type of spongy/supporting material, and which is configured to provide adequate support to the wearer, at both the upper and lower leg locations, thereby allowing one to walk using the assembled walking cast.

Referring now to FIG. 5, a perspective view is shown at 54 of a composite plastic and rigid walking cast according to a second preferred embodiment of the present invention. As best shown in each of FIGS. 5 and 7, as well as in the various two dimensional views of FIGS. 6, 8 and 9, the walking cast 54 illustrates a heavier duty wearable cast, as compared to that shown at 10 in FIG. 1, and by which the cast can replace earlier, and more unwieldy, mechanical and structural supporting casts.

The cast 54 is similar in respects to that shown at 10 and again includes a composite plastic, or other suitable rigid supporting, material. Rather than including clamshell assembleable portions (as shown in FIG. 1) the cast 54 includes a main upper cage member 56, this including a lowermost, forward positioned and arcuate extending semi-circular knee brace 58, as well as an uppermost, rearward positioned and likewise arcuate extending semi-circular thigh brace 60.

An intermediate cage brace, shown at 62, is connected by side supports 64 and 66 to the lowermost brace portion 58 and defines a support location arranged in parallel between uppermost located thigh brace 60 and lower/forward most positioned knee brace 58. A forward attachable and generally semi-cylindrical shaped forward element is generally illustrated by arcuate configured and forward located extension 67 and which is hingedly supported at an upper end by thigh brace 60 and at a lower end by the intermediate bracing support 62, thereby completely encircling the wearer's leg at the mid-thigh location.

As shown, the upper cage member 56 exhibits a generally barrel shape, with a plurality of vertically extending and spaced apart supports, at 68 and 68' (see FIG. 6), as well as at 70, 72 (see also FIG. 5) et. seq. The supports 68 and 68' as shown are rearward most extending between upper rear thigh brace 60 and intermediate rear extending intermediate brace. 62, whereas the additional vertical supports 70 and 72 (see as best shown in FIG. 8) are arranged at generally forward locations and extend between a forward and uppermost arcuate extending extension 74 (also positioned generally to the top end of the upper cage member 56 and approximate in vertical position to the upper rear thigh brace 60) and the intermediate positioned and likewise forward extending extension 67.

Figure 8:
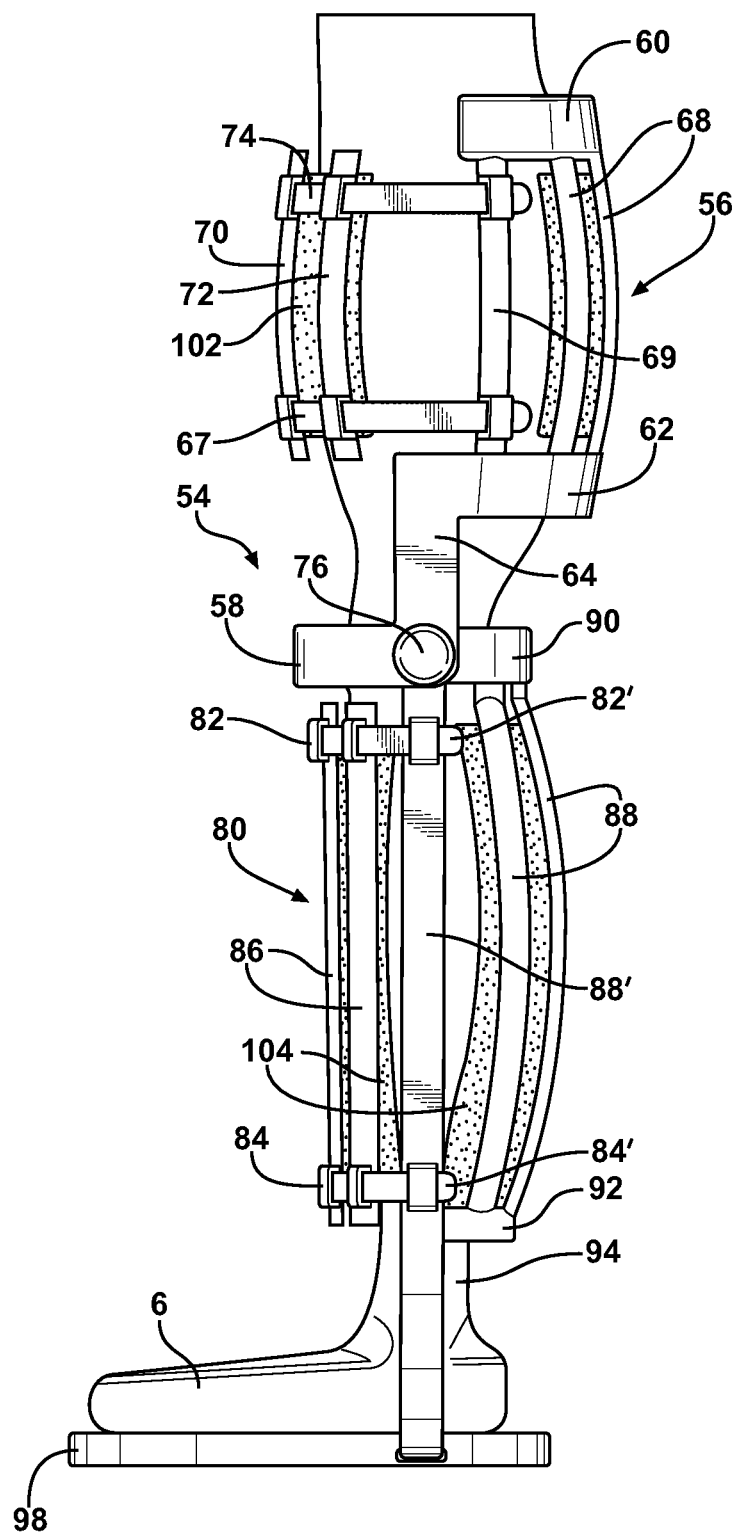
FIG. 8 is a side view of the rigid walking cast as illustrated in each of FIGS. 5-7.
Figure 9:
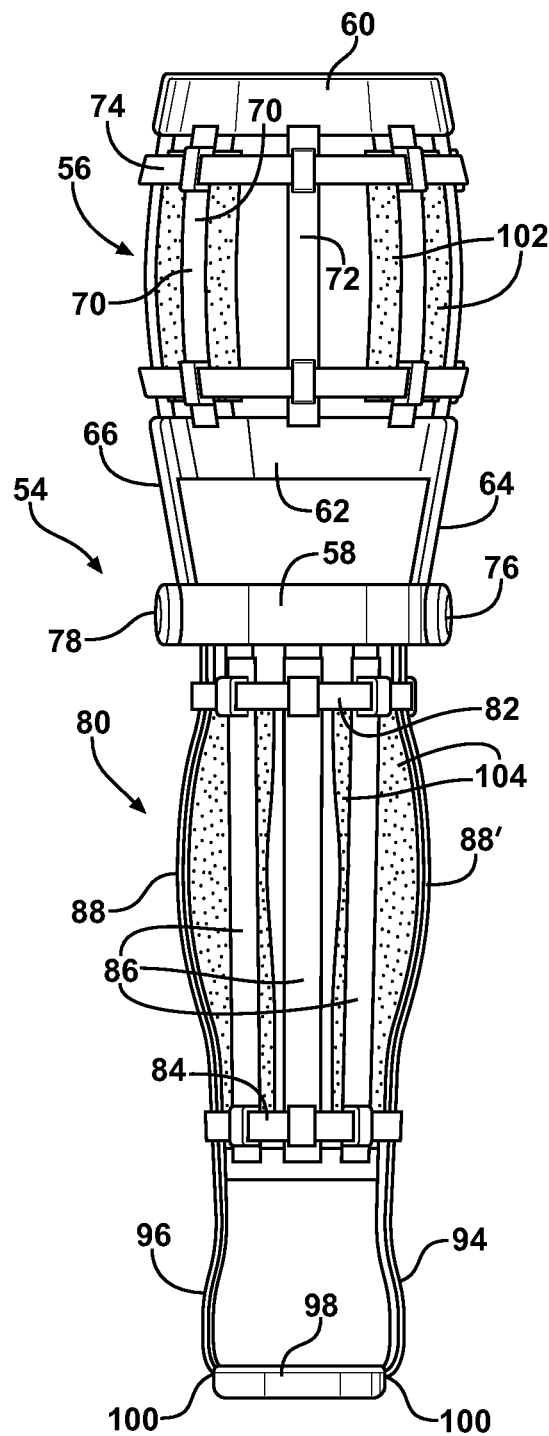
FIG. 9 is a front view of the cast shown in FIG. 5 and further illustrating the hinged nature of the second preferred embodiment.

FIG. 8 best illustrates the manner in which the forward brace including arcuate extensions 74 and 67 and vertically extending and interconnecting supports 70 and 72, define a hingedly connected and upper/forward cage portion, this being supported upon an additional fixed support 69 (again FIG. 8) similar in shape and positioning to the other fixed vertical supports 68 and likewise extending between the upper/rear thigh brace 60 and the intermediate rear brace 62 at a side-most location. Similar to the variant 10, the lowermost positioned knee brace 58 also includes a lateral most positioned hinge, this being illustrated by locations 76 and 78 and which are constructed in much the same fashion as shown by hinge locations 42 and 44 in the first variant 10.

Figure 7:
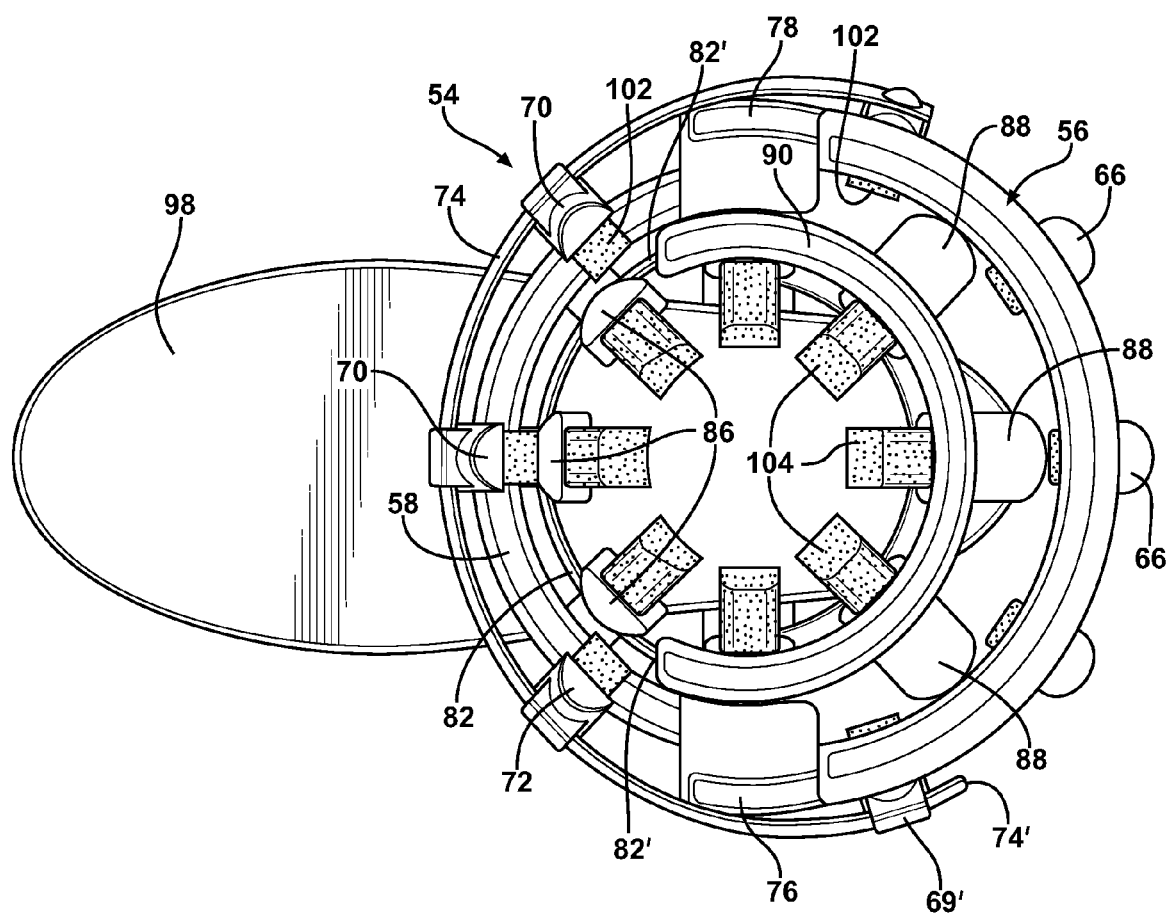
FIG. 7 is a top view of the variant of FIG. 5.

As further best shown by the top view of FIG. 7, and upon assembling the upper cage member 56, an extending strap end 74' of the brace extension 74 can be adjusted relative to a receiving location 69' associated with the additional fixed vertical support 69 (and although not shown can include such as interengaging ratchet or serrated portions or the like). Although not shown in FIG. 7, the perspective view of FIG. 6 also references the same width adjustability provided for by a lower forward brace extension location 67' and which, in combination with the adjustability aspect of the upper strap end 74', allows the upper cage member 56 to be width adjustable to support around a wearer's thigh.

A lower cage assembly is likewise shown at 80 and likewise includes a forward semi-cylindrical shaped and openable door which is composed of upper 82 and lower 84 forward and arcuate extending braces. A first plurality of generally straight, elongate and vertically extending members, see at 86, are provided and which interconnect the upper 82 and lower 84 braces. Similar to the upper cage member 56, lower cage subassembly (82, 84 and 86) is hingedly supported to a rear fixed portion of the lower assembly 80, and which further includes an additional plurality of vertically extending, and somewhat arcuate configured, members 88, these interconnecting upper 90 and lower 92 rear calf extending brace supports.

A side-most vertical member 88' defines a hinged mounting location to which the forward and pivotal cage is secured (via mounting locations 82' and 84' of the upper and lower forward brace locations as best shown in the side view of FIG. 8). Although not clearly shown, it is understood that a degree of width adjustability can also be provided at either of the upper 82' and lower 84' mounting locations and, in cooperation with the hinged nature of the connection, to facilitate easier location and fastening of both the upper and lower cage assemblies.

It is also again understood that a similar hinged engagement is provided for the variant of FIGS. 5-9, between the upper and lower cage members, and as which has been previously described in reference to FIG. 1. Reference is again made to the side view of FIG. 8, and which illustrates the hinged connection established between the lower arcuate brace 58 of the upper cage assembly and the upper (and inner seating) arcuate brace 90 of the lower cage assembly. Although not shown, it is again understood that a suitable mounting post, or projection, similar to that shown at 40 in FIG. 1, is again likewise included and which establishes the desired hinged support at the knee location.

As with the variant of FIG. 1, support to a wearer's foot 6 is provide by lower angled supports 94 and 96, these extending respectively from bottom end locations of the lower cage assembly 80 and which engage with foot sole shaped rigid support 98. Unlike the lighter duty variant of FIGS. 1-4, the variant of FIGS. 5-9 can also include a limited degree of hinged movement between the sole support 98 and the angled sides 94 and 96, this being provided at hinged locations 100 and 101 and which is established by a suitable pivotal interconnection established between the aligned sides of the sole and the engaging locations of the angled sides 94 and 96.

As best shown in FIG. 7, cushioning support is likewise provided to the second variant through the provision of individual cushioning members provided in vertically extending and individual fashion along inner extending surfaces of each of the upper cage assembly and lower cage assembly. In particular, upper vertically extending cushion supports are shown at 102 (see along inner supporting surfaces of vertical supports 68, 70, 72), whereas lower vertically extending cushion supports 104 are provided in likewise inner surface supporting fashion upon lower vertical extending members 86 and 88.

Having described my invention, other and additional preferred embodiments will become apparent to those skilled in the art to which it pertains, and without deviating from the scope of the appended claims:

I claim:
1. A walking cast adapted to be worn about a wearer's leg and for providing hinged support to the wearer's knee, said walking cast comprising:
   an upper cage having first and second assembleable sections configured to be worn over an upper leg of a wearer and extending to the wearer's thigh;
   a lower cage having first and second assembleable sections configured to be worn over a lower leg of the wearer and extending to the wearer's calf, said lower cage being hingedly secured to the upper cage approximate a wearer's knee by a pair of support posts which project in opposite and lateral fashion from upper most edge extending and arcuate shaped portions associated with said lower cage assembleable sections, said posts being received within inner seating hinges defined in overlapping and lowermost edge extending arcuate shaped portions associated with said upper and lower cage assembleable sections, such that said lower cage can be rotated relative to said upper cage at the wearer's knee and while providing support to the leg between the thigh and calf;
   each of said upper and lower cages being constructed of a rigid material exhibiting a specified shape and size, each of said sections having a plurality of interconnecting length and width extending structural supports extending between top and bottom edges of said cages which establish elongated gaps therebetween;
   upper and lower cushioning supports exhibiting interconnecting length and width extending portions which match said structural supports such that, upon securing said cushioning supports upon inner facing surfaces of said assembleable sections of said cages, said cushioning supports and structural supports collectively providing maximum breathe-ability concurrent with providing adequate conforming support to the wearers upper and lower leg; and
   a foot sole connected to the lower cage and adapted to support a wearer's foot.

2. The walking cast as described in claim 1, further comprising a pair of lower angled supports extending from said lower cage and which engage side locations of said foot sole.

3. The walking cast as described in claim 2, further comprising a hinge established between said lower angled supports and said side locations of said foot sole.

4. The walking cast as described in claim 1, further comprising at least one of said upper and lower cages being width adjustable.

5. The walking cast as described in claim 1, each of said upper and lower cages further comprising first and second assembleable and substantially semi-cylindrical sections including upper and lower pairs of mating tabs and slots for individually assembling said cages over the upper and lower leg of the wearer.

6. The walking cast as described in claim 1, each of said upper and lower cages further comprising a hingedly connecting door.

7. The walking cast as described in claim 1, further comprising arcuately angled and configured supports which define a portion of said upper cage for supporting a rear thigh of the user, while permitting the lower leg to bend an incremental degree.

8. A walking cast adapted to be worn about a wearer's leg and for providing hinged support to the wearer's knee, said walking cast comprising:

an upper cage having first and second assembleable sections configured to be worn over an upper leg of a wearer and extending to the wearer's thigh;

a lower cage having first and second assembleable sections configured to be worn over a lower leg of the wearer and extending to the wearer's calf, said lower cage being hingedly secured to the upper cage approximate a wearer's knee by a pair of support posts which project in opposite and lateral fashion from upper most edge extending and arcuate locations associated with said lower cage assembleable sections, said posts being received within inner seating hinges defined in overlapping and lowermost edge extending arcuate shaped locations associated with said upper and lower cage assembleable sections such that said lower cage can be rotated relative to said upper cage at the wearer's knee and while providing support to the leg between the thigh and calf;

each of said upper and lower cages further comprising a hingedly connecting door, each of said cages being constructed of a rigid material exhibiting grid shaped and overlapping portions so that said cast provides significant open surface area in the shape of elongated gaps extending along the wearers upper and lower leg and over the entire length of said cages;

upper and lower cushioning supports exhibiting interconnecting length and width extending portions which match said overlapping portions such that, upon securing said cushioning supports upon inner facing surfaces of said cages, said cushioning supports and cage collectively providing significant open surface area for the wearers leg while also providing adequate conforming support; and a foot sole connected to the lower cage and adapted to support a wearer's foot.

9. The walking cast as described in claim 8, further comprising a pair of lower angled supports extending from said lower cage and which engage side locations of said foot sole.

10. The walking cast as described in claim 9, further comprising a hinge established between said lower angled supports and said engaged side locations of said foot sole.

11. A walking cast adapted to be worn about a wearer's leg and for providing hinged support to the wearer's knee, said walking cast comprising:

an upper cage having first and second assembleable sections configured to be worn over an upper leg of a wearer and extending to the wearer's thigh;

a lower cage having first and second assembleable sections configured to be worn over a lower leg of the wearer and extending to the wearer's calf, said lower cage being hingedly secured to the upper cage approximate a wearer's knee by a pair of support posts which project in opposite and lateral fashion from upper most edge extending arcuate shaped portions associated with said lower cage assembleable sections, said posts being received within inner seating hinges defined in overlapping and lowermost edge extending arcuate shaped portions associated with said upper and lower cage assembleable sections, such that said lower cage can be rotated relative to said upper cage at the wearer's knee and while providing support to the leg between the thigh and calf;

each of said upper and lower cages exhibiting a generally grid shape with reinforcing and overlapping portions constructed of a rigid material and which establish elongated gaps therebetween over an entire length of said cages;

upper and lower cushioning supports exhibiting interconnecting length and width extending portions which match said overlapping portions such that, upon securing said cushioning supports upon inner facing surfaces of said cages, said cushioning supports and cage collectively providing significant open surface area for the wearers leg while also providing adequate conforming support; and a foot sole connected to the lower cage and adapted to support a wearer's foot.

12. The walking cast as described in claim 11, further comprising at least one of said upper and lower cages being width adjustable.

13. The walking cast as described in claim 11, further comprising a pair of lower angled supports extending from said lower cage and which engage side locations of said foot sole.

14. The walking cast as described in claim 11, further comprising arcuately angled and configured supports which define a portion of said upper cage for supporting a rear thigh of the user, while permitting the lower leg to bend an incremental degree.

* * * * *